(12) United States Patent
Iwamura et al.

(10) Patent No.: US 9,897,623 B2
(45) Date of Patent: Feb. 20, 2018

(54) AUTOMATIC ANALYZER

(75) Inventors: Kanako Iwamura, Otawara (JP);
Shoichi Kanayama, Otawara (JP);
Nobuyasu Kobayashi, Otawara (JP)

(73) Assignee: Toshiba Medical Systems Corporation, Otawara-shi (JP)

(*) Notice: Subject to any disclaimer, the term of this patent is extended or adjusted under 35 U.S.C. 154(b) by 0 days.

(21) Appl. No.: 12/705,149

(22) Filed: Feb. 12, 2010

(65) Prior Publication Data

US 2010/0210007 A1 Aug. 19, 2010

(30) Foreign Application Priority Data

Feb. 16, 2009 (JP) .................. 2009-032322

(51) Int. Cl.
*G01N 35/10* (2006.01)
(52) U.S. Cl.
CPC . G01N 35/1011 (2013.01); *G01N 2035/1025* (2013.01)
(58) Field of Classification Search
CPC .................. G01N 35/1009; G01N 35/1011
See application file for complete search history.

(56) References Cited

U.S. PATENT DOCUMENTS 4,818,492 A * 4/1989 Shimizu .................. 422/509

FOREIGN PATENT DOCUMENTS

| JP | 62-218818 |   | 9/1987  |
|----|-----------|---|---------|
| JP | 3-24461 A |   | 2/1991  |
| JP | 5-188060 A |  | 7/1993  |
| JP | 6-87870   |   | 12/1994 |
| JP | 10-246727 | * | 9/1998  |
| JP | 10-246727 A | | 9/1998  |
| JP | 10-256727 | * | 9/1998  |
| JP | 11-316239 |   | 11/1999 |
| JP | 2000-046843 | * | 2/2000 |
| JP | 2007-316012 | * | 6/2007 |
| JP | 2007-316013 | * | 6/2007 |
| JP | 2007-316012 |   | 12/2007 |
| JP | 2007-316013 |   | 12/2007 |

* cited by examiner

*Primary Examiner* — P. Kathryn Wright
(74) *Attorney, Agent, or Firm* — Oblon, McClelland, Maier & Neustadt, L.L.P.

(57) ABSTRACT

Disclosed is an automatic analyzer that analyzes a component of a target layer of a test sample separated into a plurality of layers by transferring the component from an installed container, including: a dispensing probe that descends into the target layer and suctions the component; a detecting unit that detects the height of the layer surface of the target layer of the test sample; a calculating unit that calculates the depth from the layer surface of the target layer at which the total content of the component of the target layer reaches a target amount; and a controller that causes the dispensing probe to descend to the depth calculated by the calculating unit and suction the component.

11 Claims, 9 Drawing Sheets

| TEST SAMPLE | MEASUREMENT ITEM A | MEASUREMENT ITEM B |
|---|---|---|
| SUBJECT ID 001 | RESULT ○○ | RESULT ✕✕ |
| ... | ... | ... |
| SUBJECT ID 006 | ERROR OF INSUFFICIENT AMOUNT OF BLOOD CELLS | RESULT △△ |
| ... | ... | ... |

AUTOMATIC ANALYZER

BACKGROUND OF THE INVENTION

1. Field of the Invention

The present invention relates to an apparatus that dispenses and stirs a test sample and reagent to measure the mixture thereof.

2. Description of the Related Art

An automatic analyzer is an apparatus that dispenses a test sample and reagent and measures the mixture thereof. After dispensing a test sample such as blood or urine and a reagent into a reaction cuvette to cause them to react, the photometry of changes in the color tone caused by the reaction provides a measurement of the concentration and activity of the measured substance or enzyme in the analyte.

This automatic analyzer has a dispensing probe that suctions the test sample and discharges it into a reaction cuvette. Once the test sample is conveyed below the dispensing probe, the dispensing probe is lowered and suctions the test sample by being subjected to negative pressure while immersed within the test sample.

For example, the total amount of collected test sample may be analyzed by the automatic analyzer. In this case, because the capacity of the test sample differs, there is a possibility that the dispensing probe may suction ineffectually if it is not lowered sufficiently. The automatic analyzer is also installed with a large number of test samples, and these test samples sequentially arrive below the dispensing probe and are sequentially suctioned and discharged, so if the dispensing probe is excessively lowered, there is a possibility that the test sample will adhere to the broad range of the outer wall surface of the dispensing probe and the adhering substance cannot be cleaned, thus causing contamination.

Thus, technology for detecting the liquid level of the test samples using an electrical resistance method, or a capacitance method, a pressure detecting method, etc. has been conventionally employed (e.g., Japanese Unexamined Patent Application Publication No. S62-218818).

Herein, in the case of measuring HbA1c (glycated hemoglobin), which is a diagnostic marker for diabetes, the automatic analyzer uses a whole blood sample as the sample to measure absorbance of the sample in which blood cell component that includes hemoglobin has been hemolyzed. In the test sample that includes this blood cell component, the blood cell component settles if left as it is, and the test sample is separated into an upper layer of plasma component and a lower layer of blood cell component. Therefore, ineffectual suction (or suction error) and contamination cannot be resolved by detecting only the liquid level.

Thus, a concept is presented in which the suction position is determined by preliminarily storing the concentration gradient of the blood cell component and estimating the depth from the liquid level to a distribution zone that includes a significant amount of blood cell component, and the dispensing probe is immersed so as to reach this distribution zone (e.g., Japanese Unexamined Patent Application Publication No. 2007-316013).

Additionally, as the shape of the container containing the test sample may differ, a concept is also presented in which the depth of the distribution zone that includes a significant amount of blood cell component is estimated from the shape of the container, the height of the liquid level, and the concentration gradient (e.g., Japanese Unexamined Patent Application Publication No. H11-316239).

However, in the case of a test sample separated into a plurality of layers, a situation of suction error should be prevented in which due to suctioning of the solution in other layers below the desired layer, collection of the test sample has to be performed again. For this purpose, the boundary between the distribution zone of the target component and the upper layer thereof, which is lowered by the suction, should not reach the tip of the dispensing probe that is a suction port by the end of suctioning. Therefore, conventionally, once the target distribution zone has been estimated, the dispensing probe enters deeper with a margin.

In order to prevent contamination, it is desirable for the entry distance of the dispensing probe into the test sample to be as small as possible so that adherence of the test sample to the outer wall surface of the dispensing probe may be reduced and cleaning may be performed sufficiently. If the entry distance is made as small as possible, the error in the suction amount can also be reduced.

However, because the technology described above only estimates the target distribution, there is a possibility that the dispensing probe will excessively enter the test sample in order to avoid suction error, thereby causing contamination. Accordingly, a considerable amount of cleaning time is spent in to ensure full cleaning.

SUMMARY OF THE INVENTION

This invention is intended to resolve the above-mentioned problem. The purpose is to provide an automatic analyzer that prevents contamination without excessive invasion of dispensing probe even if a portion except an upper layer of the test sample separated into a plurality of layers is a target layer.

A first aspect of the present invention is an automatic analyzer that analyzes a component of a target layer of a test sample separated into a plurality of layers by transferring said component from an installed container, comprising: a dispensing probe configured to lower into said target layer to suction said component; a detecting unit configured to detect the height of the layer suction error of the target layer of said test sample; a calculating unit configured to calculate the depth from the layer surface of said target layer to a position at which the total content of the component of said target layer reaches a target amount; and a controller configured to cause said dispensing probe to lower to said depth calculated by said calculating unit to suction said component.

According to the first aspect of the present invention, if the test sample is separated into a plurality of layers, the decline of the dispensing probe becomes minimum, the test sample is minimally attached to the outer wall surface of the sample-dispensing probe, and the positional relation is adjustable between the position of suctioning by the sample-dispensing probe and the border between the target layer and the upper layer at the end of suctioning. Therefore, the prevention of empty-suctioning and contamination are intended.

A second aspect of the present invention is the automatic analyzer according to the first aspect of the invention further comprising a concentration-gradient memory unit (database) configured to preliminarily store concentration gradient data representing the concentration at each depth of said component in said target layer, wherein based on said concentration gradient data, said calculating unit is configured to calculate the depth from the layer surface of said target layer to a position at which said component reaches the target amount by adding the concentrations of respective points in a depth direction.

A third aspect of the present invention is the automatic analyzer according to the second aspect of the invention further comprising a liquid properties-information memory unit configured to store liquid properties of the test sample including at least one of the hematocrit value, fibrin amount, and viscosity of said test sample as said component, wherein: said concentration-gradient memory unit is configured to preliminarily store concentration gradient data corresponding to said liquid properties information; and said calculating unit is configured to calculate said depth based on said concentration gradient data corresponding to the liquid properties of said test sample.

A fourth aspect of the present invention is the automatic analyzer according to the second aspect of the invention further comprising a patient-information memory unit configured to store patient information including at least one of the age and sex of the provider of said test sample, wherein: said concentration-gradient memory unit is configured to preliminarily store concentration gradient data corresponding to said patient information; and said calculating unit is configured to calculate said depth based on said concentration gradient data corresponding to said patient information.

A fifth aspect of the present invention is the automatic analyzer according to the second aspect of the invention, wherein: each concentration gradient over an elapsed time is stored as said concentration gradient data; and said calculating unit is configured to calculate said depth based on the concentration gradient over the elapsed time from the time when said container is installed to the time when said component is transferred.

A sixth aspect of the present invention is the automatic analyzer according to the fifth aspect of the invention, further comprising a sensor configured to sense installation of said container.

A seventh aspect of the present invention is the automatic analyzer according to the first aspect of the invention, further comprising a comparing unit configured to compare information regarding the content of said component within said target layer based on the detection results from said detecting unit with a predetermined threshold of the content of the component of said target layer, wherein said controller is configured to stop lowering to said depth and suctioning if a result of the comparison of said comparing unit indicates that the information regarding the content of said component is below said threshold.

An eighth aspect of the present invention is the automatic analyzer according to the seventh aspect of the invention, wherein said detecting unit is configured to detect the layer surface of said target layer by detecting changes in electrical resistance caused by differences between liquid layers by means of the sensor.

A ninth aspect of the present invention is the automatic analyzer according to the seventh aspect of the invention, wherein said detecting unit is configured to detect the layer surface of said target layer by detecting changes in capacitance caused by differences between liquid layers by means of the sensor.

A tenth aspect of the present invention is the automatic analyzer according to the seventh aspect of the invention, wherein said detecting unit is configured to detect the layer surface of said target layer by detecting changes in pressure or viscosity caused by differences between liquid layers by means of the sensor.

An eleventh aspect of the present invention is the automatic analyzer according to the eighth aspect of the invention, further comprising a threshold memory unit configured to store various thresholds for the total content of the component of said target layer corresponding to the type information of each said container, wherein said comparing unit is configured to compare said threshold corresponding to the type information with said height by obtaining the type information of said container containing said test sample.

A twelfth aspect of the present invention is the automatic analyzer according to the seventh aspect of the invention, wherein, if the information regarding the content of said component is below said threshold, said comparing unit is configured to cause an error indicating a content insufficiency to be stored corresponding to said test sample.

A thirteenth aspect of the present invention is an automatic analyzer that analyzes a component of a target layer of a test sample separated into a plurality of layers by transferring said component from an installed container, comprising: a dispensing probe configured to lower into said target layer and suction said component; a concentration-gradient memory unit configured to preliminarily store concentration gradient data representing the concentration at each depth of said component within said target layer corresponding to elapsed time from the time when said container is installed to the time when said component is transferred; a calculating unit configured to calculate the depth from the layer surface of said target layer to a position at which said component reaches a target amount by adding concentrations at respective points in a depth direction, based on the concentration gradient data over said elapsed time; and a controller configured to cause said dispensing probe to lower to said depth calculated by said calculating unit to suction said component.

DETAILED DESCRIPTION OF THE EMBODIMENTS (Configuration)

An apparatus according to embodiments of the present invention will be described with reference to the figures.

Figure 1:
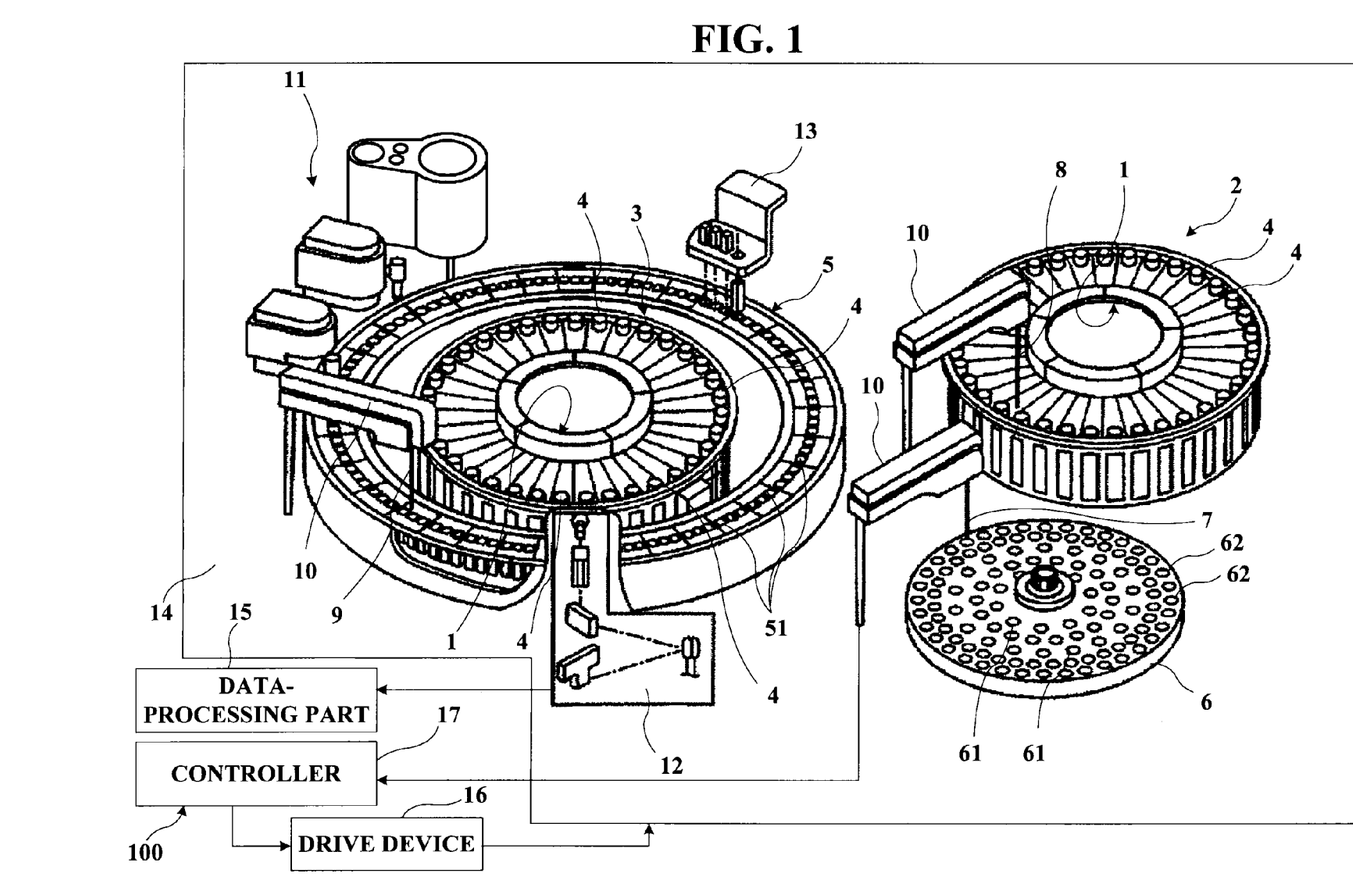
FIG. 1 shows the structure of the automatic analyzer.

The automatic analyzer 100 shown in FIG. 1 is an apparatus that dispenses a test sample and a reagent and analyzes the mixture thereof, thereby analyzing the chemical component contained in the test sample.

After transferring a test sample such as blood or urine and the reagent into a reaction tube (cuvette) 51 to cause them to react, the photometry of changes in the color tone caused by the reaction provides a measurement of the concentration and activity of the measured substance or enzyme in the analyte.

This automatic analyzer 100 mainly has an analyzing part 14, a data-processing part 15, a drive device 16, and a controller 17.

The analyzing part 14 dispenses the test sample and reagent for analyzing the reaction of the mixture thereof and outputs resulting measurement data. The data-processing part 15 processes the resulting measurement data outputted by the analyzing part 14 to generate standard curve data and analysis data and outputs the data to a monitor and printer equipped therewith. The drive device 16 is configured so as to include a motor and gears, etc. and drives each unit in the analyzing part 14 by generating a drive force and transmitting the force to each unit in the analyzing part 14. The controller 17 controls the drive of each unit included in the analyzing part 14, as described below.

The test sample directed for analysis by the automatic analyzer 100 is a liquid matter such as blood or urine. The reagent is a liquid chemical that chemically reacts with the component contained in the test sample.

The present embodiment will be described by using blood as the test sample and taking the measurement of the blood cell component as an example. However, the present invention is applicable to any liquid as long as the liquid separates into a plurality of layers over time for reasons such as sedimentation, for example, and it may also be applicable to the measurement of erythrocytes, leukocytes, or platelets.

This test sample is contained in the sample container 61. The sample container 61 is installed on a rotatable circular disc sampler 6.

A sensor 62 that senses installment of the test sample is disposed in each installed position on the disc sampler 6. Examples of the sensor 62 include an optical sensor, on which a light-emitting element and a light-receiving element are oppositely disposed so as to sandwich the installed position of the sample container 61.

Alternatively, it is a pressure sensor positioned on the bottom surface of the installed position of the sample container 61.

Once the sample container 61 is installed, this sensor 62 outputs a signal that indicates installment to the controller 17. The signal outputted by the sensor 62 marks the start of the elapsed time from the time at which the test sample contained in the container 61 is set on the automatic analyzer 100 until the time when it is dispensed into the reaction tube (cuvette) 51. That is, the signal indicates the starting point when separation of the liquid layer begins.

The reagent is contained in a reagent container 4. The reagent container 4 is installed on the reagent storage 2 and reagent storage 3.

The reagent container 4 contains various first reagents that selectively react to the item to be measured of the test sample, or various second reagents corresponding to the first reagent. The reagent container 4 containing the first reagent is installed on the reagent storage 2, while the reagent container 4 containing the second reagent is installed on the reagent storage 3.

A rotatable circular reagent rack 1 is stored in the reagent storage 2 and reagent storage 3. Each reagent container 4 is circularly stored in this reagent rack 1 side by side.

The reaction tube (cuvette) 51 into which the test sample and reagent are discharged is circularly installed on a rotatable circular reaction disc 5 side by side.

Dispensing of the test sample and reagent is performed by a sample-dispensing probe 7, a first reagent-dispensing probe 8, and a second reagent-dispensing probe 9.

The sample-dispensing probe 7 is erected near the disc sampler 6 and the reaction disc 5. This sample-dispensing probe 7 suctions the test sample from the sample container 61 conveyed to a given suction position via rotation of the disc sampler 6, and discharges the test sample into the reaction tube (cuvette) 51 conveyed to the discharging position via rotation of the reaction disc 5.

The first reagent-dispensing probe 8 is erected near the reagent storage 2 and the reaction disc 5. The first reagent-dispensing probe 8 suctions the first sample from the reagent container 4 conveyed to a given suction position via rotation of the reagent rack 1 of the reagent storage 2, and discharges the first reagent into the reaction tube (cuvette) 51 conveyed to a given discharging position via rotation of the reaction disc 5.

The second reagent-dispensing probe 9 is erected near the reagent storage 3 and the reaction disc 5. The second reagent-dispensing probe 9 suctions the second reagent from the reagent container 4 conveyed to a given suction position via rotation of the reagent rack 1 of the reagent storage 3, and discharges the second reagent into the reaction tube (cuvette) 51 conveyed to a given discharging position via rotation of the reaction disc 5.

Furthermore, a stirring unit 11, a photometry unit 12, and a cleaning unit 13 are erected on the periphery of the reaction disc 5.

The reaction disc 51 into which the test sample and reagent have been dispensed is conveyed to the stirring, measuring, and washing positions of the stirring unit 11, photometry unit 12, and washing unit 13, respectively, according to the order of rotation of the reaction disc 5.

The stirring unit 11 is a stirring part that stirs, for each cycle, the mixture, such as the test sample+first reagent and the test sample+first reagent+second reagent, within the reaction tube (cuvette) 51 that has been stopped at the stirring position.

The photometry unit 12 is a measuring part that measures, from the photometry position, the mixture contained the reaction tube (cuvette) 51. The photometry unit 12 has light sources and a light-receiving part, which are positioned so as to sandwich the reaction tube (cuvette) 51, and for example, outputs that resulting measurement data to the data-processing part 15 after photometry of the absorbance of the mixture.

The washing unit 13 suctions the mixture for which measurement has been completed within the reaction tube (cuvette) 51 that has been stopped at the washing and drying position, while washing and drying the inside of the reaction tube (cuvette) 51.

Figure 2:
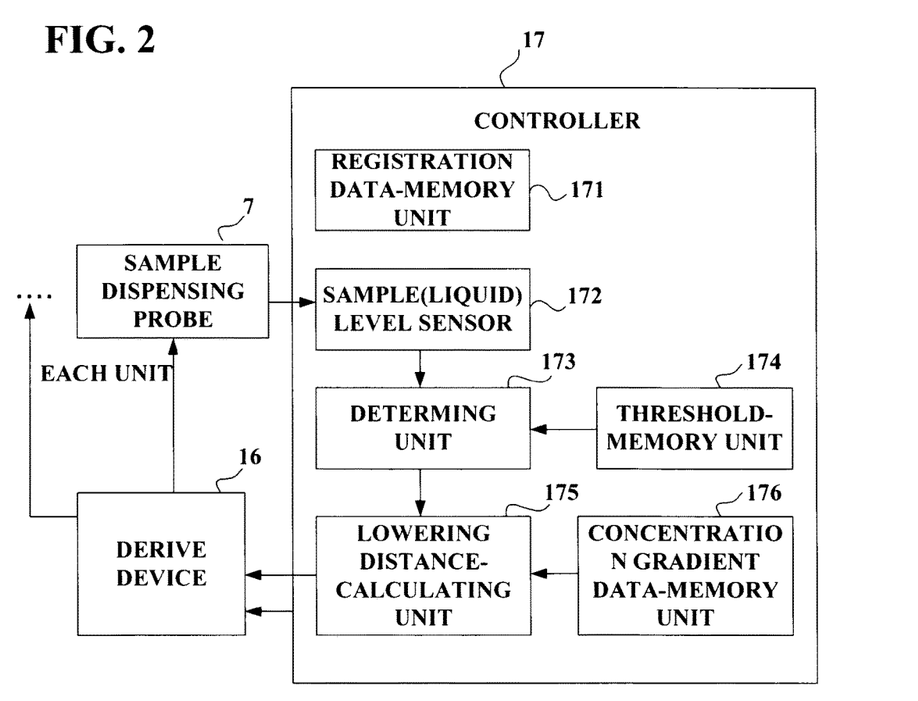
FIG. 2 shows a detailed structure of a controller.
Figure 3:
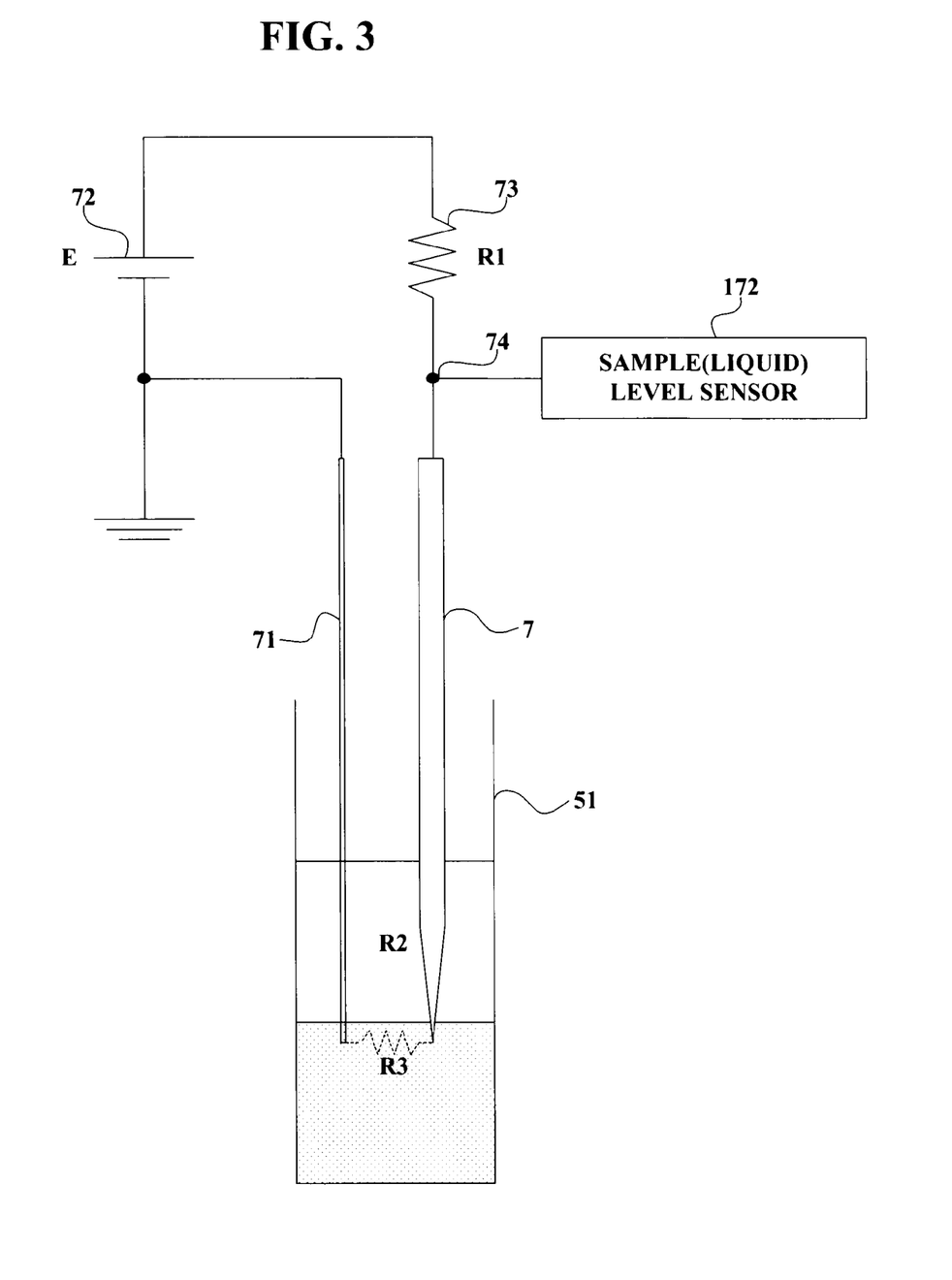
FIG. 3 shows a structure of a sample-dispensing probe.

For such an automatic analyzer 100, the control of each unit performed by the controller 17, especially control of the sample-dispensing probe 7, will be described based on FIG. 2 and FIG. 3. FIG. 2 is a block diagram showing a detailed configuration of the controller 17. FIG. 3 is a diagram showing the configuration of the sample-dispensing probe 7.

First, the controller 17 causes the disc sampler 6, the reagent rack 1 of the reagent storage 2, and the reagent rack 1 of the reagent storage 3 to rotate for each cycle to thereby convey the test sample and the reagent to a given suction position.

At the time of rotating the disc sampler 6, the reagent rack 1 of the reagent storage 2, and the reagent rack 1 of the reagent storage 3, this controller 17 refers to registration data stored in a registration data-memory unit 171.

The registration data-memory unit 171 stores, as test sample data, the age and sex of the subject that is the provider of the test sample, the position at which the test sample is installed, the position at which the first reagent is installed, the position at which the second reagent is installed, the reaction tube (cuvette) 51 into which the test sample is dispensed, the item to be measured for the test sample, and the type of first reagent and second reagent used according to the item to be measured. The test sample data is registered using an inputting part such as a keyboard and mouse positioned on the console of the automatic analyzer 100.

Once the reaction tube (cuvette) 51 is conveyed to the position for discharging the test sample, the controller 17 refers to the registered data and causes the disc sampler 6 to rotate until the sample container 61 containing the test sample that is dispensed into the reaction tube (cuvette) 51 is moved to the position for suction by the sample-dispensing probe 7.

Additionally, once the reaction tube (cuvette) 51 is conveyed to the position for discharging the first reagent, the controller 17 refers to the registered data and causes the reagent rack 1 of the reagent storage 2 to rotate until the reagent container 4 containing the first reagent that is dispensed into the reaction tube (cuvette) 51 is moved to the position for suction by the first reagent-dispensing probe 8.

Additionally, once the reaction tube (cuvette) 51 is conveyed to the position for discharging the second reagent, the controller 17 refers to the registered data and causes the reagent rack 1 of the reagent storage 3 to rotate until the reagent container 4 containing the second reagent that is dispensed into the reaction tube (cuvette) 51 is moved to the position for suction by the second reagent-dispensing probe 9.

This controller 17 has a sample (liquid) level sensor 172, a determining unit 173, a threshold-memory unit 174, a lowering distance-calculating unit 175, and a concentration gradient memory unit 176 for controlling the sample-dispensing probe 7.

The test sample is separated into an upper layer of the plasma layer and a lower layer of the blood cell layer over time or by centrifugation. This controller 17 detects the layer surface (plane) of the blood cell layer to determine whether the content of blood cells reaches the target amount. If it is determined that the target amount is contained, the controller 17 calculates the minimum lowering distance for the sample-dispensing probe 7 to suction the amount of blood cells required for analysis and causes the sample-dispensing probe 7 to be lowered according to the minimum lowering distance.

Herein, the sample-dispensing probe 7 is a so-called straw attached to an arm 10 as shown in FIG. 3 and suctions and discharges the test sample and reagent via negative and positive pressures generated by a pump (not shown).

The arm 10 is capable of independent axial rotation and extension by the drive force transmitted from the drive device 16 through a gear, etc. The axis rotation of the arm 10 allows for the sample-dispensing probe 7 to move to given suctioning and discharging positions. Additionally, extension of the arm 10 also allows for the sample-dispensing probe 7 to be lifted and lowered for suctioning and discharging.

The sample-dispensing probe 7 includes a conductor such as stainless steel or platinum. Furthermore, a probe 71 that includes a conductor such as stainless steel or platinum is suspended from the arm 10 to the same height as the tip of the sample-dispensing probe 7.

The sample-dispensing probe 7 and probe 71 constitute a pair of electrodes and are connected to power sources 72 that apply direct voltage, for example.

Once these sample-dispensing probe 7 and probe 71 are immersed into the test sample, conductivity is provided between the electrodes by being mediated by the immersed liquid layer.

Figure 4:
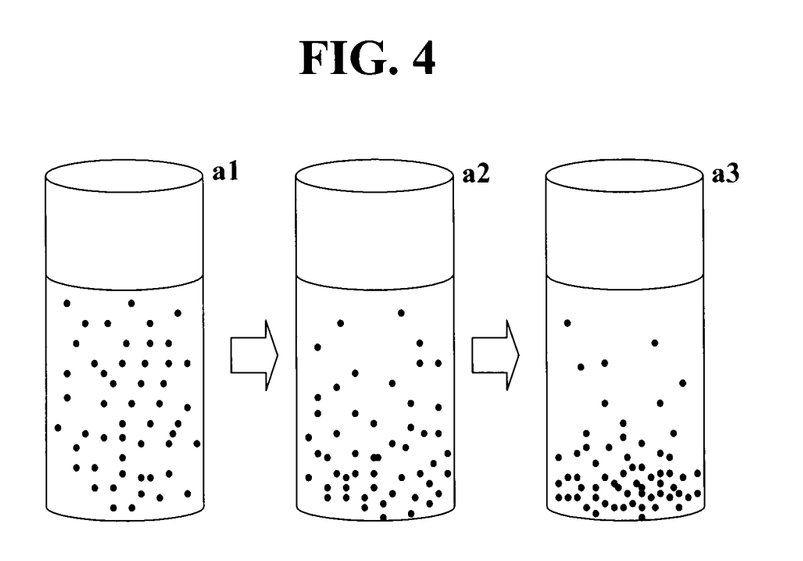
FIG. 4 shows a state of a blood cell component included in an obtained sample settling.

In the test sample, the blood cell component settles over time as shown in FIG. 4, and the test sample is separated into an upper layer in which the blood cell component is below a certain level and plasma is the main component, and a lower layer in which the blood cell component is above a certain level. This is because the specific gravity of the blood cell component is higher than the plasma component.

Therefore, for example, it is assumed that resistance 73 having a resistance value R1 is interposed between the power sources 72 and the sample-dispensing probe 7 and that the probe 71 is grounded. Then, when the sample-dispensing probe 7 and probe 71 contact the liquid level after the test sample begins to separate into upper and lower layers, assuming that the voltage value outputted by the power sources 72 is E and that the electrical resistance value of the liquid layer in which the blood cell component is below a certain level and the plasma component is a main component is R2, the voltage value V1 of a reference point 74 set between the resistance 73 and the sample-dispensing probe 7 is determined by V1=E×R2/(R1+R2).

Furthermore, when the sample-dispensing probe 7 and probe 71 contact the lower layer in which the blood cell component of the test sample is above a certain level, assuming that the electrical resistance value of the lower layer is R3, the voltage value V2 of the reference point 74 set between the resistance 73 and the sample-dispensing probe 7 is determined by V2=E×R3/(R1+R3).

The sample (liquid) level sensor 172 of the controller 17 uses changes in the voltage value of the reference point 74 caused by this contact of the liquid layer to detect that the tip of the sample-dispensing probe 7 has reached the liquid layer of the blood cell component and outputs the height of that liquid layer.

This sample (liquid) level sensor 172 preliminarily has a threshold potential Vs2 for detecting the voltage value V2. If the voltage value of the reference point 74 is the threshold potential Vs2, the sample (liquid) level sensor 172 calculates, from the distance for lowering the sample-dispensing probe 7 at that time, the height from the bottom of the reaction tube (cuvette) 51 to the upper surface of the liquid layer of the blood cell component, and outputs this height of the liquid layer. The distance for lowering the sample-dispensing probe 7 is obtained from the value outputted, for example, by an encoder or potentiometer equipped in the drive device 16.

The determining unit 173 determines whether the blood cell component contains the target amount. When the volume or bottom area of the reaction tube (cuvette) 51 is preliminarily known, the component amount of the blood cell depends on the height of the liquid layer of the component. The threshold-memory unit 174 preliminarily stores the threshold for the height, and the determining unit 173 retrieves this threshold and compares the threshold with the height outputted by the sample (liquid) level sensor 172.

If the height outputted by the sample (liquid) level sensor 172 is below the threshold, the determining unit 173 generates an error indication that indicates that the blood cell component is insufficient.

Moreover, the determining unit 173 compares the threshold with the height of the liquid layer of the blood cell component, as information regarding the content of the blood cell component.

Alternatively, the amount of blood cell component using the concentration gradient data 177 as described below, and the amount of liquid layer of the blood cell component may be used as information regarding the content of the blood cell component. In this case, the threshold-memory unit 174 preliminarily stores the threshold for the component amount corresponding to the amount of blood cell component, and the threshold for the liquid amount corresponding to the amount of the blood cell component liquid layer.

When the shape of the reaction tube (cuvette) 51 installed on the automatic analyzer 100 is not uniform, that is, when differently shaped tube (cuvette)s and certain kinds of reaction tube (cuvette)s 51 can be installed on the automatic analyzer 100, the threshold-memory unit 174 stores the respective thresholds corresponding to various types of type information representing the shape of the reaction tube (cuvette) 51.

The description of the type information is provided to the reaction tube (cuvette) 51 via a barcode etc. The determining unit 173 controls a retrieving device, etc. so as to obtain the type information that has been read by the barcode, etc. of the reaction tube (cuvette) 51 and uses the threshold corresponding to the obtained type information as a comparison object.

The lowering distance-calculating unit 175 calculates the minimum lowering distance from the layer surface of the blood cell component when it is determined that a sufficient amount of blood cell component can be suctioned for analysis. The minimum lowering distance is a minimum required lowering distance for suctioning the required amount of blood cell component.

Figure 5:
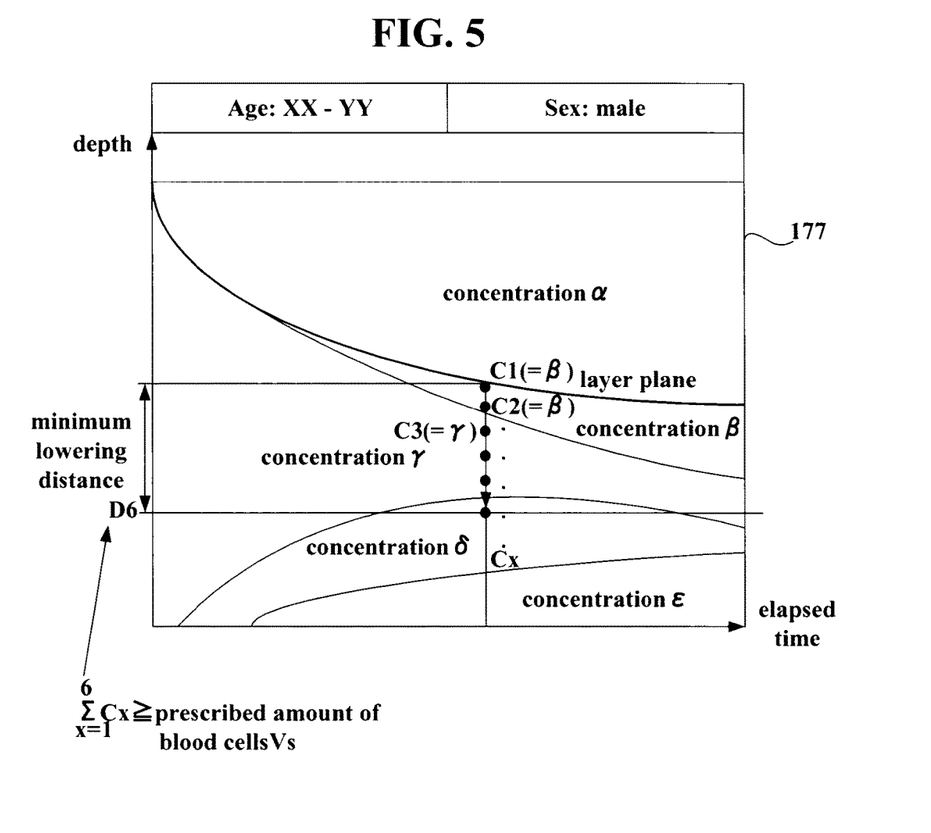
FIG. 5 shows a schematic diagram on a concentration gradient data.

In order to calculate the minimum lowering distance, the concentration gradient data 177 is referenced, which is stored in the concentration gradient data-memory unit 176. The concentration gradient data 177 is data arranged 2-dimensionally that is the value of the concentration of blood cell component at each point as shown in FIG. 5, assuming that the horizontal axis represents the elapsed time and the vertical axis represents the depth. In other words, the concentration gradient data 177 represents the concentration of the blood cell component at which a certain period of time has elapsed.

The concentration gradient of the blood cell component depends on the age and sex of the subject. The concentration gradient data-memory unit 176 stores the concentration gradient data 177 for each age and sex. The concentration gradient data 177 that matches the age and sex of the test sample stored in the registration data-memory unit 171 is selected.

The lowering distance-calculating unit 175 selectively uses the concentration gradient data 177 for each given distance in order to integrate the concentration value Cx (x=1, 2, 3, . . . ) in the depth direction from the height corresponding to the layer surface of the blood cell component. For example, the distance by the depth D6 (=given distance×(6−1)) at which the total content ΣCx (e.g., x=1 to 6) has reached the predetermined target amount (erythrocyte amount) Vs is measured as the lowering distance.

The integrated concentration value Cx is the value at each point in the elapsed time from the time when the test sample was installed on the disc sampler 6 until the time when the test sample reaches the sample-dispensing probe 7.

The elapsed time is derived by subtracting the time when the sensor 62 equipped in the disc sampler 6 outputs a signal indicating installation of the sample container 61, from the time when the test sample reaches the sample-dispensing probe 7.

Once the lowering distance is calculated, the controller 17 controls the drive device 16 so as to lower the sample-dispensing probe by the lowering distance calculated via the lowering distance-calculating unit 175 and controls the pump to perform suction.

(Operations)

Figure 6:
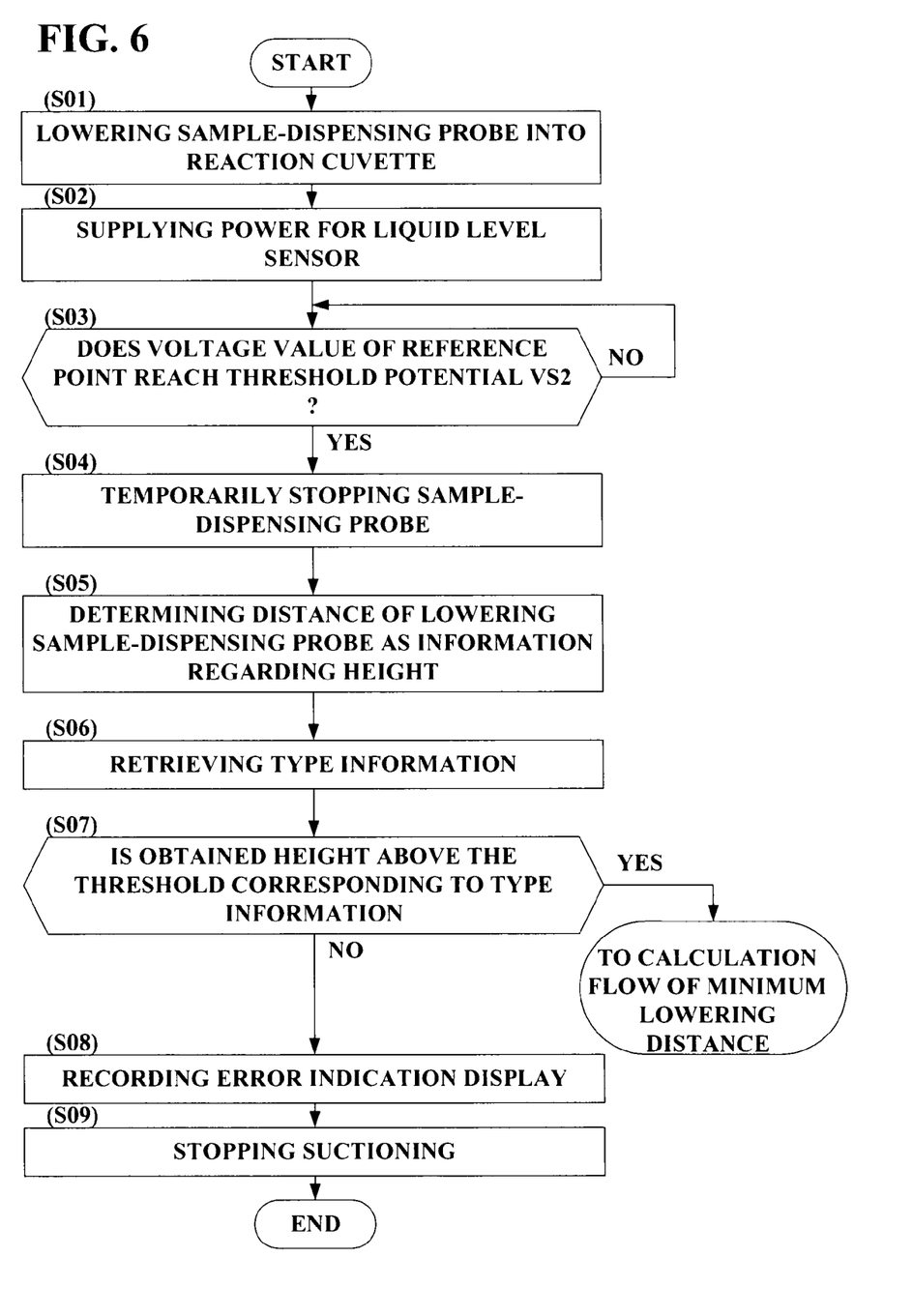
FIG. 6 shows a flowchart of detecting a liquid layer.

The operation for detecting the liquid layer by this controller 17 will now be described. FIG. 6 is a flowchart showing the operation for detecting the liquid layer.

First, the controller 17 causes the sample-dispensing probe 7 to be lowered into the reaction tube (cuvette) 51 by driving the drive device 16 of the arm 10 that supports the sample-dispensing probe 7 (S01).

Once the sample-dispensing probe 7 begins to lower, the sample (liquid) level sensor 172 causes the power sources 72 to supply power (S02) and compares the voltage value of the reference point 74 with the threshold potential Vs2 (S03). If the voltage value of the reference point 74 does not decrease to the threshold potential Vs2 (S03, No), S03 is repeated for each specific period.

On the other hand, if the voltage value of the reference point 74 reaches the threshold potential Vs2 (S03, Yes), the sample (liquid) level sensor 172 temporarily stops the sample-dispensing probe 7 (S04) and determines the distance of lowering the sample-dispensing probe 7 as information regarding the height (S05).

Once the distance for lowering the sample-dispensing probe 7 is determined, the determining unit 173 determines whether the height of the lower layer in which the blood cell component is above a certain level is above a given height.

Figure 7A:
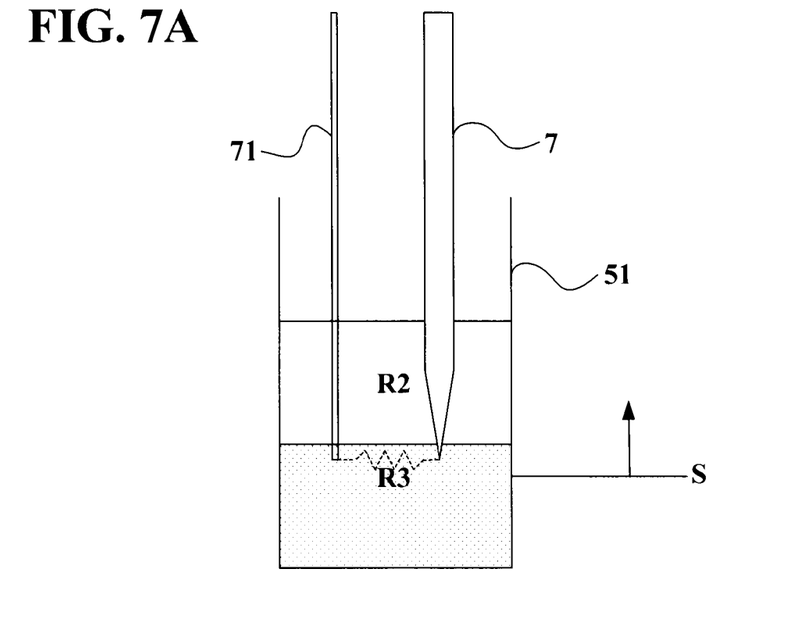
FIG. 7A shows determination of an amount of blood cell components, which is particularly equal to or more than a certain level.

In this determination, the determining unit 173 first retrieves the type information from the barcode of the reaction tube (cuvette) 51 (S06) and retrieves, from the threshold-memory unit 174, the threshold S corresponding to the type information (S07). Then, as shown in FIG. 7A, if the height of the lower layer in which the blood cell component is above a certain level is above the threshold S (S07, Yes), the determining unit 173 completes the process and switches to a calculation flow of the minimum lowering distance as described below (refer to FIG. 9). Meanwhile, when it is assumed that the uniform reaction tube (cuvette) 51 is used, steps S06 to S07 are omitted.

Figure 7B:
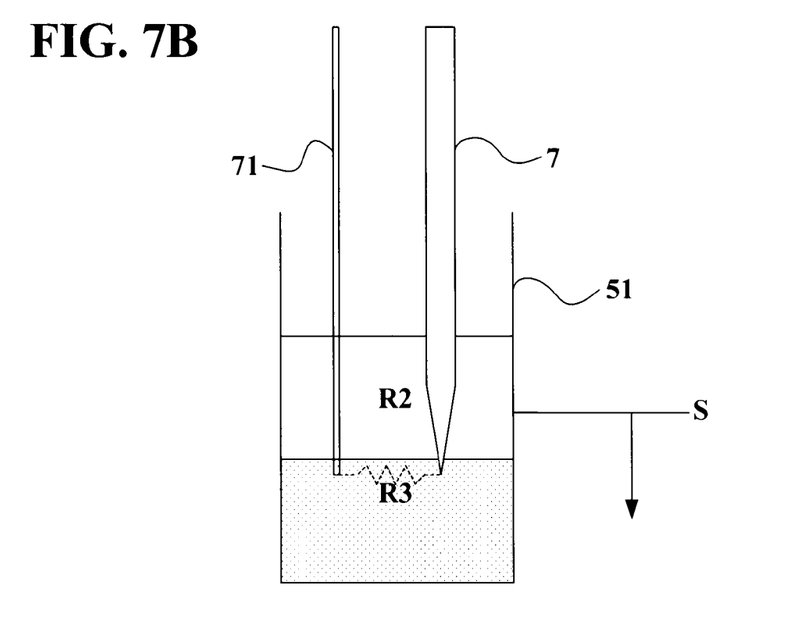
FIG. 7B shows determination of an amount of blood cell components, which is particularly below a certain level.
Figure 8:
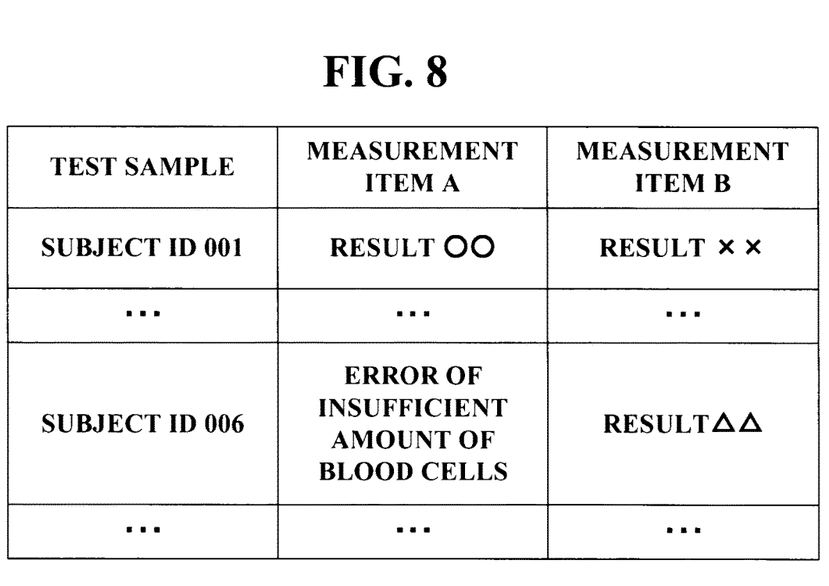
FIG. 8 shows an error indication when an amount of blood cell components does not reach a certain level.

On the other hand, as shown in FIG. 7B, if the height of the lower layer in which the blood cell component is above a certain level is below the threshold S (S07, No), the determining unit 173 records the error indication by matching the error indication with the item to be measured regarding the blood cell component of the test sample (S08). This error indication can be displayed on a monitor, etc. as shown in FIG. 8.

Furthermore, the determining unit 173 causes the sample-dispensing probe 7 to stop suctioning of the blood cell component (S09). In other words, the determining unit 173 causes the sample-dispensing probe 7 to be lifted by driving the drive device 16.

Figure 9:
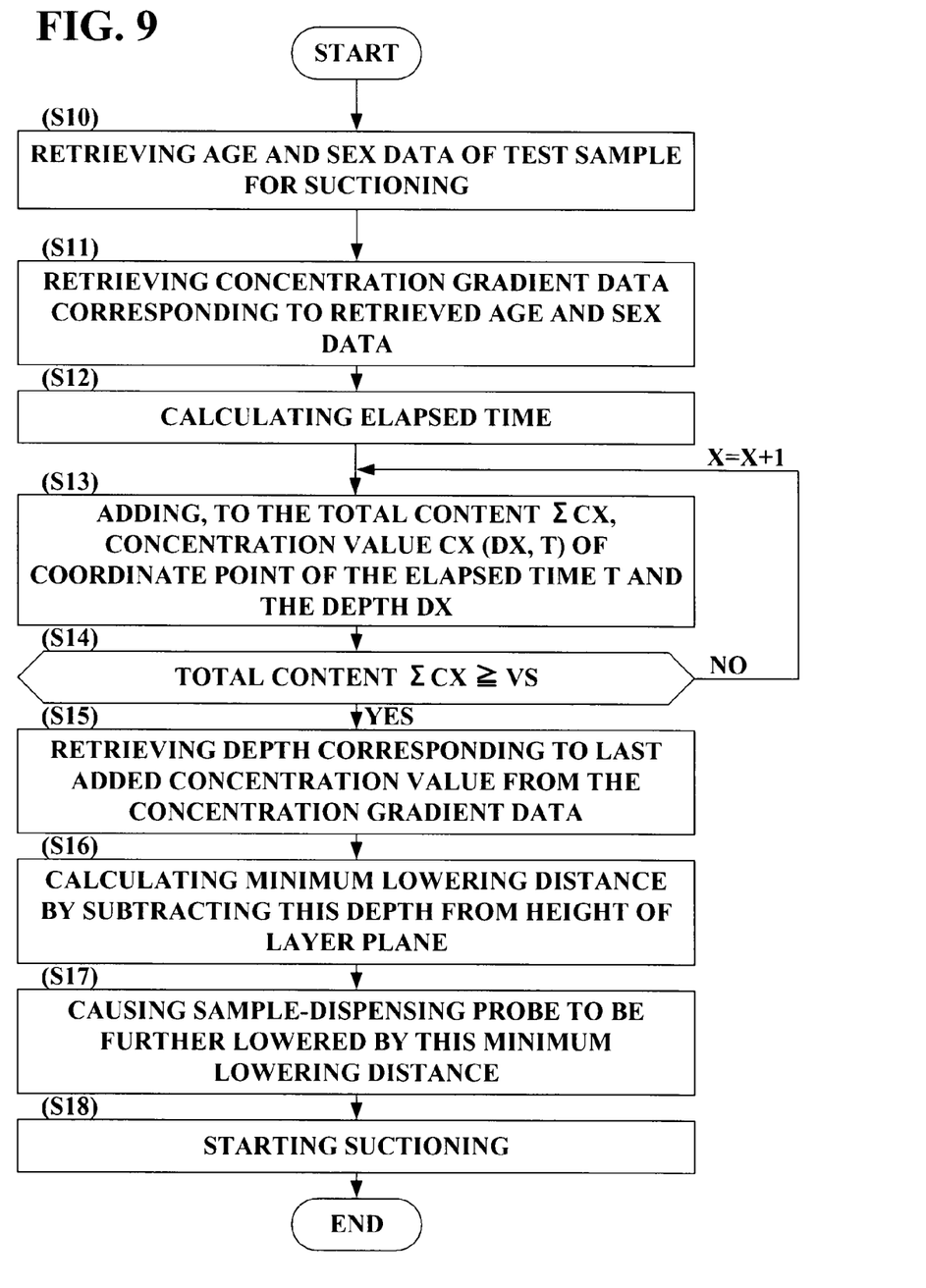
FIG. 9 shows a flowchart of calculating a declining distance of the sample dispensing probe.

Then, the operation for calculating the lowering distance by which this controller 17 causes the sample-dispensing probe 7 to be lowered will be described, wherein the height of the lower layer in which the blood cell component is above a certain level is above the threshold. FIG. 9 is a flowchart showing the operation for calculating the lowering distance.

First, if the height of the lower layer in which the blood cell component is above a certain level is above the threshold (S07, Yes), as a result of the determination performed by the determining unit 173, the lowering distance-calculating unit 175 performs selection of the concentration gradient data 177.

In the selection of the concentration gradient data 177, the lowering distance-calculating unit 175 retrieves the age and sex data of the test sample for suctioning, from the registration data-memory unit 171 (S10). Then, the lowering distance-calculating unit 175 retrieves the concentration gradient data 177 corresponding to the retrieved age and sex data, from the concentration gradient data-memory unit 176 (S11).

Once the concentration gradient data 177 is retrieved, the lowering distance-calculating unit 175 calculates the elapsed time T. In the calculation of the elapsed time T, the lowering distance-calculating unit 175 subtracts the time when the sensor 62 outputs a signal from the time when the test sample is conveyed to the position for suctioning by the sample-dispensing probe 7 (S12).

Then, the lowering distance-calculating unit 175 refers to the concentration gradient data 177 as shown FIG. 5 in order to integrate the concentration value Cx at each point corresponding to the calculated elapsed time T, in the depth direction from the height of the layer surface (plane) in which the blood cell component is above a certain level. In this integration, the lowering distance-calculating unit 175 starts, from a point on surface layer, the concentration value Cx at each point on the line indicating "the elapsed time T=constant", and sequentially integrates in the depth direction.

In other words, the lowering distance-calculating unit 175 adds, to the total content $\Sigma Cx$, the concentration value Cx (Dx, T) of the coordinate point of the elapsed time T and the depth Dx of the layer surface (plane) in the concentration gradient data 177 (S13), and if the total content $\Sigma Cx$ does not reach the predetermined target amount Vs (S14, No), it returns to S13 and adds the concentration value Cx (Dx, T), that is to be x=x+1, to the total content $\Sigma Cx$.

On the other hand, if the total content $\Sigma Cx$ reaches the predetermined target amount Vs (S14, Yes), the lowering distance-calculating unit 175 sets the lowering depth to the depth Dx (i.e., D6) corresponding to the last added concentration value Cx (e.g., X=6) (S15).

Then, the lowering distance-calculating unit 175 calculates the minimum lowering distance by subtracting this depth Dx from the height of the lower layer in which the blood cell component is above a certain level (S16) and causes the sample-dispensing probe 7 to be further lowered by this minimum lowering distance by driving the drive device 16 (S17).

Once lowering is completed, the controller 17 causes the sample-dispensing probe 7 to start suctioning by driving the pump (not shown) (S18).

In this way, in the process in which the component of the target layer in the test sample separated into a plurality of layers is dispensed from the sample container 61, this automatic analyzer 100 calculates the depth until the total content of the component from the layer surface of the target layer reaches the target amount Vs and causes the sample-dispensing probe 7 to be lowered to the calculated depth to initiate suction.

In the calculation of the depth, for example, the concentration gradient data 177 for the component in the target layer is preliminarily stored and, based on this concentration gradient data 177, the concentration value Cx at each depth from the layer surface of the target layer is added until reaching the target amount Vs.

Accordingly, even if the test sample is separated into a plurality of layers, it is possible to minimize the lowering of the sample-dispensing probe 7, thereby minimizing adherence of the test sample to the outer wall surface of the sample-dispensing probe 7 and enabling adjustment of the positional relationship between the boundary of the upper layer and target layer, and the suction port of the sample-dispensing probe 7 at the end of suctioning. Thus, it is possible for it to be designed to avoid empty-suction and prevent contamination.

In order to optimize the minimum lowering distance, the concentration gradient data 177 corresponding to each age is preliminarily stored, and the depth may be calculated based on the concentration gradient data 177 corresponding to the age of the provider of the test sample. Additionally, the concentration gradient data 177 corresponding to each sex is preliminarily stored, and the depth may be calculated based on the concentration gradient data 177 corresponding to the sex of the provider of the test sample.

For example, hemoglobin is classified into the three types HbA, HbA2, and HbF according to the difference in the globin portion, which is a component. HbF refers to embryonic hemoglobin, which occupies 80% of the total hemoglobin immediately after birth and gradually decreases to the value typical of an adult around the age of 5 years. HbA1c is hemoglobin in which glucose is bound to hemoglobin HbA, the value of which is represented as a percentage relative to the total amount of hemoglobin.

Therefore, the blood cell component differs according to age and sex of the subject, and different compositions of the blood cell component have different concentration gradients of the blood cell component. Consequently, the minimum lowering distance can be calculated more accurately by using the concentration gradient data 177 corresponding to each age, thus further preventing contamination.

Furthermore, in order to optimize the minimum lowering distance, the concentration gradient data 177 is preliminarily stored, which records each concentration gradient corresponding to the elapsed time, and the depth may be calculated based on the concentration gradient corresponding to the elapsed time T from the time of installation of the sample container 61 until the time of dispensing.

The elapsed time is measured, for example, by being equipped with a sensor 62 that detects installment of the sample container 61.

This automatic analyzer 100 also comprises the sample (liquid) level sensor 172 that detects the target layer of the test sample contained in the sample container 61 and compares, with the threshold, the information regarding the content within the target layer, based on detection by the sample (liquid) level sensor 172, and as a result of the comparison, if the information regarding the content of the component is below the threshold, lowering and suctioning are stopped and it is stored in association with the test sample so as to display an error indicating an insufficient amount. Examples of information regarding the content of the component include the height of the layer surface (plane).

Therefore, if the amount of the test sample is too small for analyzing the test sample, as in the case of a whole blood test, adherence of the test sample to the sample-dispensing probe 7 can be reduced, thus enabling the prevention of contamination.

When the shape of the sample container 61 is not uniform, various thresholds may be stored corresponding to the information of the various types of sample containers 61 so as to obtain the type information of the sample container 61 containing the test sample and to compare the threshold corresponding to that type information with the height.

In the present embodiment, the electrical resistance method has been used for detecting the liquid layer. Alternatively, a capacitance method or a method using the pressure and viscosity of the liquid may be applicable as long as the layer surface (plane) of the lower layer can be detected.

For example, the capacitance method can use the sample-dispensing probe 7 as the capacitance sensor and detect the layer surface from changes in capacitance caused by contact between the sample-dispensing probe 7 and the test sample. Alternatively, it is also possible to detect the layer surface from changes in liquid properties, such as the pressure or viscosity, by configuring it so that the tip of the sample-dispensing probe 7 and the tip of the pressure sensor or viscosity sensor are at the same height and that they move synchronously.

Furthermore, the layer surface of the lower layer may be estimated from the depth ratio of a boundary point above a given concentration value, which can be derived from the concentration gradient data, relative to the liquid level by detecting the liquid level of the test sample.

Furthermore, according to the above-described embodiment, the lowering distance-calculating unit 175 refers to the concentration gradient data 177 (horizontal axis: elapsed time, longitudinal axis: depth, as shown by FIG. 5) preliminarily stored in the concentration gradient data-memory unit 176 to add concentration data in the direction of depth to determine the depth (the minimum lowering mount) until the amount of the component reaches a target value.

However, the concentration gradient data 177 is not limited to this feature, and may be a table stored with correspondence of the elapsed time, the depth (the minimum lowering amount) and the concentration. Alternatively, the concentration gradient data 177 may be a database providing the table with correspondence of the liquid property such as the viscosity and the hematocrit, and the patient information such as the gender, the age, the medical history. If the concentration gradient data 177 is a table or a database as described above, "to add concentration data in the direction of depth" means that the lowering distance-calculating unit 175 refers to the table to determine the concentration based on the elapsed time. Further, "to determine the depth (the minimum lowering mount)" means referring to the table to determine the depth (the minimum lowering mount) corresponding to the determined concentration".

Other Embodiments

Next, an apparatus according to other embodiments of the present invention will be described. In the above embodiment, a calculating unit has been described that calculates the depth from the layer surface of the target layer, based on the concentration gradient data corresponding to the patient information including the age and/or the sex of the provider of the test sample, but not limited to this, the apparatus may comprise: a liquid properties-memory unit that stores the liquid properties of the test sample including at least one value among the hematocrit value, fibrin amount, and viscosity of the test sample; and the concentration-gradient memory unit that preliminarily stores the concentration gradient data corresponding to the liquid properties, wherein the calculating unit calculates the depth from the layer surface of the target layer, based on the concentration gradient data corresponding to the liquid properties of the test sample.

The hematocrit value is a numerical value representing the ratio of the volume of blood cells in the blood. The blood viscosity and the hematocrit value have a significant positive correlation. It is known that the higher the number of erythrocytes and the hematocrit value is, the higher will be the blood viscosity. The higher the blood viscosity is, the slower will be the sedimentation, so the correlation between the hematocrit value and the concentration gradient data can be obtained.

Fibrin is a scleroprotein that is produced via the action of fibrinogen with thrombin in coagulation of the blood. The larger the fibrin amount is, the slower will be the sedimentation, so as with the hematocrit value, the correlation between the fibrin amount and the concentration gradient data can be obtained.

Generally, the hematocrit value of the test sample is preliminarily measured by an external device in the case of a medical checkup of the subject. The controller 17 receives the input operation performed by the inputting unit and causes the liquid properties-memory unit to store the preliminarily measured hematocrit value. The calculating unit (lowering distance-calculating unit 175) receives the instruction from the controller 17 and calculates the depth from the layer surface of the target layer, based on the concentration gradient data corresponding to the hematocrit value of the test sample retrieved from the concentration-gradient memory unit (concentration gradient data-memory unit 176).

The case of the fibrin amount and viscosity is similar to the case of hematocrit value. Specifically, the controller 17 receives the input operation performed by the operation part (not shown) and causes the liquid properties-memory unit to store the preliminarily measured fibrin amount or viscosity. The calculating unit (lowering distance-calculating unit 175) receives the instruction from the controller 17 and calculates the depth from the layer surface of the target layer, based on the concentration gradient data corresponding to the fibrin amount or viscosity of the test sample retrieved from the concentration-gradient memory unit (concentration gradient data-memory unit 176).

What is claimed is:

1. An automatic analyzer that suctions a test sample from a sample and discharges the sample into a container of predetermined volume or size to produce a reaction between the test sample and a reagent, comprising:
    a dispensing probe configured to lower into a target layer of the sample separated into a plurality of layers to suction component in the target layer as the test sample;
    a photometer to measure changes of the reaction; and
    a controller configured to include:
    a concentration-gradient memory unit configured to preliminarily store concentration gradient data representing the concentration at a depth of said component in said target layer;
    a sample level sensor to detect a layer surface of said target layer; and
    a lowering-distance calculating unit configured to calculate a lowering distance from the layer surface of said target layer by adding concentrations of respective points in a depth direction from the layer surface of said target layer to obtain a totally contained amount, and to compare the totally contained amount with a target amount of suctioning a component in the target layer, the lowering distance being calculated as a depth when the totally contained amount reaches the target amount, wherein the controller is configured to cause said dispensing probe to lower based on said lowering distance calculated by said lowering-distance calculating unit to suction said component;

the controller is configured to include a determining unit to determine a volume of the target layer using the known volume or size of the container and a height of the surface of the target layer relative to the container determined by the sample level sensor; and the lowering-distance calculating unit uses the concentration data comprising concentration of the component as a function of depth in the volume of the target layer to determine the totally contained amount of the component.

2. The automatic analyzer according to claim 1, wherein the lowering-distance calculating unit integrates concentration to determine the totally contained amount.

3. The automatic analyzer according to claim 1, further comprising a patient-information memory unit configured to store patient information including at least one of the age and sex of the provider of said test sample, wherein:

said concentration-gradient memory unit is configured to preliminarily store said concentration gradient data corresponding to said patient information; and said calculating unit is configured to calculate said depth based on said concentration gradient data corresponding to said patient information.

4. The automatic analyzer according to claim 1, wherein:

each concentration gradient over an elapsed time is stored as said concentration gradient data; and said calculating unit is configured to calculate said depth based on the concentration gradient over the elapsed time from a time when said container is installed to a time when said component is transferred.

5. The automatic analyzer according to claim 4, further comprising a sensor configured to sense installation of said container.

6. The automatic analyzer according to claim 1, wherein said determining unit is configured to compare information regarding content of said component within said target layer with a predetermined threshold of the content of the component of said target layer, and said controller is configured to stop lowering to said depth and suctioning if a result of the comparison of said determining unit indicates that the information regarding the content of said component is below said threshold.

7. The automatic analyzer according to claim 6, wherein said sample level sensor is configured to detect the layer surface of said target layer by detecting changes in electrical resistance caused by differences between liquid layers by means of a sensor.

8. The automatic analyzer according to claim 6, wherein said sample level sensor is configured to detect the layer surface of said target layer by detecting changes in capacitance caused by differences between liquid layers by means of a capacitive sensor.

9. The automatic analyzer according to claim 6, wherein said sample level sensor is configured to detect the layer surface of said target layer by detecting changes in pressure or viscosity caused by differences between liquid layers by means of a sensor.

10. The automatic analyzer according to claim 7, wherein said controller is further configured to include a threshold memory unit configured to store various thresholds for the total content of the component of said target layer corresponding to type information of each said container, wherein said determining unit is configured to compare said threshold corresponding to the type information with said height by obtaining the type information of said container containing said test sample.

11. The automatic analyzer according to claim 6, wherein, if the information regarding the content of said component is below said threshold, said determining unit is configured to cause an error indicating a content insufficiency to be stored corresponding to said test sample.

* * * * *